United States Patent [19]

Soll

[11] Patent Number: 5,464,827
[45] Date of Patent: Nov. 7, 1995

[54] ESTERIFIED POLYANIONIC CYCLODEXTRINS AS SMOOTH MUSCLE CELL PROLIFERATION INHIBITORS

[75] Inventor: Richard M. Soll, Lawrenceville, N.J.

[73] Assignee: American Home Products Corporation, Madison, N.J.

[21] Appl. No.: 263,691

[22] Filed: Jun. 20, 1994

[51] Int. Cl.$^6$ ............................ A61K 31/70; C08B 37/02
[52] U.S. Cl. ............................................. 514/58; 536/103
[58] Field of Search ........................... 549/415; 536/103; 514/58

[56] References Cited

U.S. PATENT DOCUMENTS 5,019,562  5/1991  Folkman ................................. 514/58

FOREIGN PATENT DOCUMENTS 9309790  5/1993  WIPO.

OTHER PUBLICATIONS

McCaffrey et al., Biochem. Biophys. Res. Comm. 184(2), 773–781 (1992).
Paul et al., Thrombosis Research 46, 793–801 (1987).
Clowes and Reidy, J. Vasc. Surg., 885–891 (1991).
Castellot et al., Seminars in Thrombosis and Hemostasis 13(4), 489–503 (1987).
Herrmann et al., Arteriosclerosis and Thrombosis 13(6), 924–931 (1993).
Reilly et al., Drug Development Research 29, 137–147 (1993).
Pukao et al., Amer. J. Pathology 139(6), 1501–1509 (1991).
Weisz et al., Angiogenesis: Key Principles, pp. 107–117, Birkhauser 1992.
Boisson–Vidal et al., Drugs of the Future 16(6), 539–545 (1991).
Ross, Nature 362, 801–809 (1993).
Tiozzo et al., Arzneim.–Forsch/Drug Res. 39(1), 15–20 (1989).

*Primary Examiner*—Nicky Chan
*Attorney, Agent, or Firm*—Robert F. Boswell, Jr.

[57] ABSTRACT

This invention relates esterified polysulfated cyclodextrins, their use in treating diseases and conditions which are characterized by excessive smooth muscle cell (SMC) proliferation such as restenosis and a pharmaceutical composition thereof. The compounds useful in this invention are represented by Formula I:

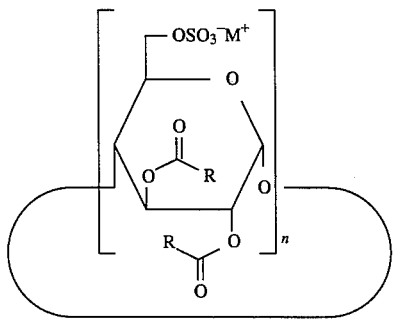

where:
M is a pharmaceutically acceptable cation;
R is selected from the group consisting of $C_1$–$C_{12}$ lower alkyl, $C_3$–$C_{12}$ cycloalkyl, and aryl optionally substituted with 1–3 substituents independently selected from halogen, $C_1$–$C_{12}$ lower alkyl or $C_1$–$C_{12}$ alkoxy; and
n is an integer from 6–8, representing α-cyclodextrin (n=6), β-cyclodextrin (n=7), and γ-cyclodextrin (n=8).

9 Claims, No Drawings

ESTERIFIED POLYANIONIC CYCLODEXTRINS AS SMOOTH MUSCLE CELL PROLIFERATION INHIBITORS

FIELD OF INVENTION

This invention relates esterified polysulfated cyclodextrins, their use in treating diseases and conditions which are characterized by excessive smooth muscle cell (SMC) proliferation such as restenosis and a pharmaceutical composition thereof.

BACKGROUND OF INVENTION

Smooth muscle proliferation has been implicated as a critical event in the development of stenosis following vascular reconstruction (e.g. percutaneous translumenal angioplasty), transplantation arteriosclerosis, and atherosclerosis (Ross, R. *Nature* 1993, 362, 801; Clowes, A. W.; Reidy, M. A. *J. Vasc. Surg* 1991, 13, 885). Pharmacological approaches to SMC proliferation inhibitors for the treatment of these states have included heparin and its fragments, (Castellot, J. J. Jr.; Wright, T. C.; Karnovsky, M. J. *Seminars in Thrombosis and Hemostasis* 1987, 13, 489), low molecular weight heparins (Tiozzo, R.; Cingi, M. R.; Tietrangelo, A.; Albertazzi, L.; Calandra, S.; Milani, M. R. *Arzneim-Forsch./Drug Res.* 1989, 39, 15), and heparin-mimicking agents (heparinoids) such as pentosan polysulfate, and fucoidan (Paul, R.; Herbert, J. M.; Maffrand, J. P.; Lansen, J.; Modat, G.; Pereillo, J. M.; Gordon, J. L. *Thrombosis Research* 1987, 46, 793; McCaffrey, T. A.; Falcone, D. J.; Borth, W.; Brayton, C. F.; Weskler, B. B. *Biochem. Biophys. Res. Commun.* 1992, 184, 773). However, many heparinoids, like heparin and heparin fragments, are heterogeneous, polymeric, highly anionic polysaccharides, most of which still retain significant anticoagulant activity (Maffrand, J. P.; Herbert, M. M.; Bernat, A.; Defreyn, G.; Delevassee, D.; Savi, P.; Pinot, J. J.; Sampol, J. *Seminars in Thrombosis and Hemostasis* 1991, 17 (Suppl. 2), 186; Boisson-Vidal, C; Colliec-Jouault, S.; Fisher, A. M.; Tapon-Bretaudiere, J.; Sternberg, C.; Durand, P.; Jozefonvicz, J. *Drugs of the Furture* 1991, 16, 539; Colliec, S.; Fischer, A. M.; Tapon-Bretaudiere, J.; Boisson, C.; Durand, P.; Jozefonvicz, J. *Thrombosis Research* 1991, 64, 143). SMC antiproliferative polyanionic compounds which possess well defined structure would not only be homogeneous in composition but would also be expected to inhibit smooth muscle proliferation without the liabilities, such as anticoagulant effects, associated with heparin and heparinoids.

Beta-Cyclodextrin tetradecasulfate has been described as a smooth muscle cell proliferation inhibitor and as an effective inhibitor of restenosis (Weisz, P. B.; Hermann, H. C.; Joullie, M. M.; Kumor, K.; Levine, E. M.; Macarak, E. J.; Weiner, D. B. *Angiogenesis: Key Principle-Science-Technology-Medicine-* Steiner R., Weisz, P. B.; Langer, R. Eds. Birkhauser Verlag, Basel Switzerland, 1992, pg. 107; Hermann, H. C.; Okada, S. S.; Hozakowska, E.; LeVeen, R. F.; Golden, M. A.; Tomaszewski J. E.; Weisz, P. B.; Barnathan E. S. *Arteriosclerosis and Thrombosis* 1993, 13,924; Reilly, C. F.; Fujita, T.; McFall, R. C.; Stabilito, I. I.; Wai-si E.; Johnson, R. G. *Drug Development Research* 1993, 29, 137. The closest prior art is disclosed in U.S. Pat. No. 5,019,562 and WO 93/09790. U.S. Pat. No. 5,019,562 discloses anionic derivatives of cyclodextrins administered concurrently with cortisone for treating pathological conditions associated with undesirable cell or tissue growth. WO 93/09790 discloses antiproliferative polyanionic derivatives of cyclodextrins bearing from 2 to 24 anionic residues per cyclodextrin monomer unit. The present invention differs from all of the above mentioned prior art in that it discloses well defined, modified, polyanionic cyclodextrin derivatives which (a) bear exactly one anionic group per sugar residue at a specific position and (b) are further modified by neutral, lipophilic esters.

DESCRIPTION OF THE INVENTION

This invention describes the composition and utility of well defined, C-6 sulfated, C-2, C-3-esterified cyclodextrin derivatives of general formula I

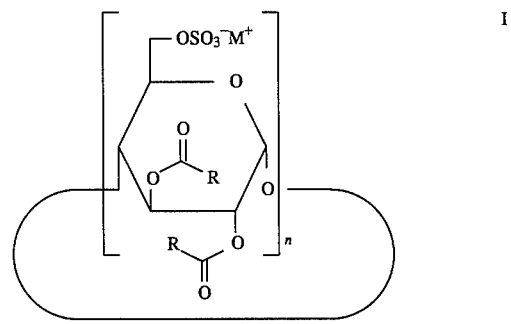

where:

M is a pharmaceutically acceptable cation;

R is selected from the group consisting of $C_1$–$C_{12}$ lower alkyl, $C_3$–$C_{12}$ cycloalkyl, and aryl optionally substituted with 1–3 substituents independently selected from halogen, $C_1$–$C_{12}$ lower alkyl or $C_1$–$C_{12}$ alkoxy; and n is an integer from 6–8, representing α-cyclodextrin (n=6), β-cyclodextrin (n=7), and γ-cyclodextrin (n=8).

The more preferred compounds of this invention are those wherein:

M is a pharmaceutically acceptable cation;

R is selected from the group consisting of $C_1$–$C_{12}$ loweralkyl, $C_3$–$C_{12}$ cycloalkyl, and aryl; and n is an integer from 6–8, representing α-cyclodextrin (n=6), β-cyclodextrin (n=7), and γ-cyclodextrin (n=8).

Still more preferred compounds of this invention are those wherein

M is a pharmaceutically acceptable salt cation;

R is phenyl; and n is an integer from 6–8, representing α-cyclodextrin (n=6), β-cyclodextrin (n=7), and γ-cyclodextrin (n=8);

The most preferred compound of this invention is one wherein:

M is a Na;

R is phenyl; and n is 6.

The term $C_1$–$C_{12}$ lower alkyl encompasses straight and branched chain alkyl groups having from one to twelve carbons. The term $C_1$–$C_{12}$ alkoxy is an —O—$C_1$–$C_{12}$ lower alkyl where the $C_1$–$C_{12}$ lower alkyl group is as defined above. The term aryl means phenyl, 1-naphthyl or 2-naphthyl and the aryl group may be substituted with one to three substituents selected independently from halogen, $C_1$–$C_{12}$ lower alkyl or $C_1$–$C_{12}$ alkoxy. The term halogen means fluorine, chlorine, bromine or iodine. The term pharmaceutically acceptable cation means an alkali metal cation, alkaline earth cation, or an ammonium cation such as Na+, K+, Ca+ or tetra-n-butylammonium cation.

As evidenced by the most preferred compound of this invention, the compounds of Formula I act as low molecular weight heparin mimics, exhibiting pronounced smooth muscle cell antiproliferation activity with little anticoagulant liability. Compounds which act to inhibit smooth muscle cell proliferation are useful for diseases which are characterized by excessive smooth muscle cell proliferation which arise most frequently from vascular reconstructive surgery and transplantation, i.e., balloon angioplasty, vascular graft surgery, coronary artery bypass surgery, and heart transplantation. Other disease states in which there is unwanted vascular proliferation include hypertension, o asthma, and congestive heart failure. Thus this invention provides novel compounds and a method of treating diseases caused by smooth muscle cell proliferation. This invention further provides for a pharmaceutical composition for treating diseases attributed to smooth muscle cell proliferation.

DETAILED DESCRIPTION OF THE INVENTION

The compounds of general formula I may be obtained by standard procedures of organic chemistry well known in the art. For example, compounds of general formula IV can be prepared using the procedures described by Boger et. al. (*Helv. Chim. Acta* 1978, 61, 2190). The alcohols III are then sulfated using excess standard sulfating agents, for example sulfur trioxide trimethyl amine complex, in a solvent such as dimethylformamide or dimethylsulfoxide with heating up to 95° C. for a period of up to two days. The trialkylammonium salts are conveniently convened to appropriate salts for example, sodium salt using a conventional cation exchange resin.

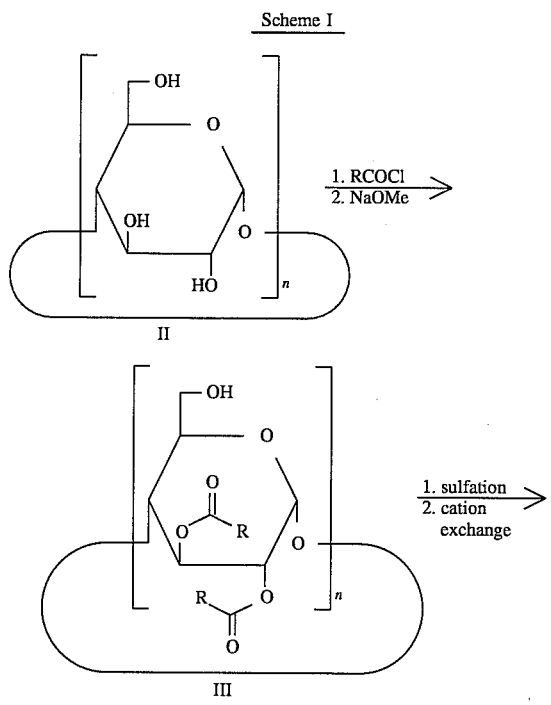

Scheme I

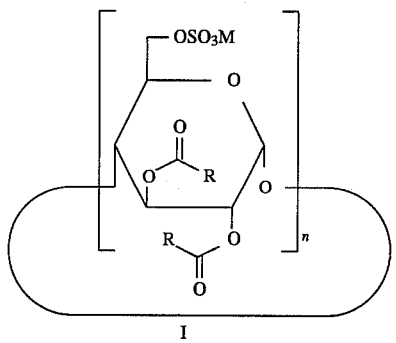

-continued
Scheme I

A specific procedure is described in the following example. This example is given to illustrate the invention and should not be construed as limiting the invention in any way.

Preparation of α-Cyclodextrin- 2A, 2B, 2C, 2D, 2E, 2F, 3A, 3B, 3C, 3D, 3E, 3F-Dodeca-O-Benzoyl-6A, 6B, 6C, 6D, 6E, 6F-Hexa-O-Sulfato-α-Cyclodextrin Hexasodium Salt To 500 mg (0.225 mmol) of α-cyclodextrin- 2A, 2B, 2C, 2D, 2E, 2F, 3A, 3B, 3C, 3D, 3E, 3F-dodeca-O-benzoate (Boger, J.; Corcoran, J.; Lehn, J. M. *Helv. Chim. Acta* 1978, 61, 2190) in 25 mL of DMF was added 1.7 g (12.2 mmol) of sulfur trioxide trimethylamine complex. The reaction mixture was stirred at 70° C. overnight. The reaction mixture was concentrated and quenched with 50 mL of methanol and ethanol. The solvent was removed in vacuo. The residue was suspended in MeOH and filtered. The filtrate was concentrated and then the residue was purified by flash chromatography [MeOH: THF: $NEt_3$ (1: 1:0.1) and then MeOH:$NEt_3$ (10: 1)]. The solid residue was dissolved in MeOH/$CH_2Cl_2$ (1: 1) and filtered to remove particulates. The filtrate was concentrated to give 710 mg of a tan powder. A solution of 500 mg of the powder in methanol was passed through a Dowex resin column (50×8 strongly acidic, Na form) using MeOH elution to give 370 mg of a pale tan powder after removal of solvent (in vacuo). The residue was dissolved in a mixture of toluene and methanol and triturated with petroleum ether to give 339 mg of a colorless solid, mp 191°–193° C. (dec): $^1$H-NMR ($d_6$-DMSO; 400 Mz) δ7.46 (d, 2H), 7.32 (d, 2H), 7.24 (t, 1H), 7.06 (t, 2H), 6.87 (t, 2H), 6.11 (t, 1H), 5.54 (d, 1H; J=2.7 Hz), 4.92 (dd, 1H), 4.65 (d, 1H), 4.50 (d, 1H), and 4.26–4.34 ppm(m, 2H); $^{13}$C-NMR ($d_6$DMSO; 100 Mz) 165.06, 164.43, 132.72, 132.51,129.24, 129.01, 128.93, 127.93, 127.87, 127.68, 95.81, 75.52, 72.02, 71.65, 70.44, 65.08 ppm; mass spectrum ((−) FAB) m/e 2810 (M—Na), 2708 (M—Na—$SO_3$+H), 2606 (M—2Na—2$SO_3$+2H): IR (KBr) 1725 $cm^{-1}$. Anal. Calcd. for $C_{120}H_{102}Na_6O_{60}S_6$.8 $H_2O$: C, 48.39; H, 4.00; S, 6.45 Found: C, 48.13; H, 3.98; S, 6.13. Purity and homogeneity was determined using reverse phase HPLC (Novapax C18), eluting with 78, MeOH, 22% 0.005M n-$Bu_4NHSO_4$ at a flow rate of 1 mL/min and $UV_{254}$ detection.

Pharmacology

The ability of the compounds of the present invention to inhibit smooth muscle cell proliferation was established using isolated porcine-derived, smooth muscle cells. Porcine aortas were received from a local slaughterhouse. The material was iced during transit. The aorta was scrupulously cleansed of fatty tissue and rinsed in sterile phosphate-buffered saline with 2% antibiotic/antimycotic (Gibco catalog #600-5240 AG). The tissue was then digested in 10–15 ml of "Enzyme Mixture" containing collagenase type I, 165 U/mL; elastase type III, 15 U/mL; BSA, 2 mg/mL; and soybean trypsin inhibttor, 0.375 mg/mL followed by incubation at 37° under 5% $CO_2$ for 10–15 minutes. After this treatment, the outer surface adventitia was easily removed by peeling with forceps The aorta was then longitudinally cut and laid open and the endothelial layer was removed by scraping.

The medical layer of cells was rinsed in enzyme solution, and placed in a new 100 mm dish with 10 mL enzyme solution. The aorta was minced using a fine pair of scissors and digested for 2–3 hours at 37° in 30 ml of fresh enzyme solution. After digestion, the tissue was homogenized using a sterile Pasteur pipette with a fire polished tip or an eppendorf pipetter with a 200–1000 ml sterile pipette tip. The suspension was then centrifuged for 10 minutes at 8000 rpm and the pellet was suspended in 4–6 mls of fresh medium and plated onto 4–6 100 mm flasks with vented caps. Cells were allowed to grow to confluence and split using 0.25 % trypsin. Cells were evaluated foe purity and overall quality using antibody to SMC actin. Cells were only evaluated for growth characteristics in early passage (P2–P7).

In general, primary cell cultures were grown in 16 mm multiwell culture dishes in media 199 supplemented with 10% fetal bovine serum and 2% antibiotic/antimycotic. At subconfluence, the cells were placed in a defined serum free medium for 24–48 hour containing (Aim-V; Gibco) supplemented with 10% FBS, 2% antibiotic/antimycotic, and 0.5 μci/mL $^3$H-thymidine. Total volume was 1 mL per well. Test compounds were added to each well at 50 fold dilution (20 μL/well) and the plates were incubated for 24–36 hours at 37° C. in 5% $CO_2$. Test compounds were diluted in DMSO, ethanol or $H_2O$ depending on solubility. Compounds found to be insoluble in any solvent were routinely heated for a period of 5–10 minutes and/or sonicated to achieve dissolution. As a control, grade II porcine intestinal mucosal heparin (sodium salt) from Sigma (H-7005) was routinely assayed in porcine cell preparations at concentrations from 0.1 to 100 μg/ml.

Plates were then placed on ice, washed three times with ice cold PBS and incubated in ice cold 10% trichloroacetic acid (TCA) for 30 minutes to remove acid soluble proteins. 24-well plates were then treated with 0.4N NaOH (500 μL/well) overnight at room temperature. Solution was transferred to scintillation vials containing 0.4N HCL (500 μl/vial to neutralize NaOH) and each well was rinsed two times with water (500 μL) for a total volume of 2 ml/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data is expressed as a percent of control. For example, the compound of example 1 inhibited porcine smooth muscle cell proliferation with an $IC_{50}$ value of 7.05 μg/ml. By comparison, α-cyclodextrin sulfate (D.S.=12) and β-cyclodextrin tetradecasulfate (D.S.= 14), both of which were purchased through American Maize Company, Hammond, Ind., inhibited smooth muscle cell proliferation with $IC_{50}$ values of 421 μg/ml and 95.8 μg/ml, respectively.

The anticlotting activity of the compounds of this invention were evaluated in a partial thromboplastin time (APTT) assay using normal human plasma. A BBL Fibrometer automatic precision coagulation timer utilizing a 0.3 ml probe was employed. For example, No significant difference effect on the APTT was observed with the compound of example 1 at concentrations of 25 μg/ml–100 μg/ml in comparison to control thereby demonstrating little anticlotting activity.

Pharmaceutical administration

The compounds of this invention may be administered systemically, for example by intravenous injection, typically ranging from 0.1 to 10 mg/kg/hr over 5–30 days, or by subcutaneous injection at lower dose, by oral administration at higher dose than intravenous injection. Localized delivery of the compounds of this invention may also be achieved by transmembrane, transdermal, or other topical administrative routes using appropriate continuous release devices such as supporting matrix, where applicable. The compositions of the invention may be formulated with conventional excipients, such as a filler, a disintegrating agent, a binder, a lubricant, a flavoring agent and the like. These are formulated in a conventional manner.

What is claimed is:

1. A compound of Formula I below

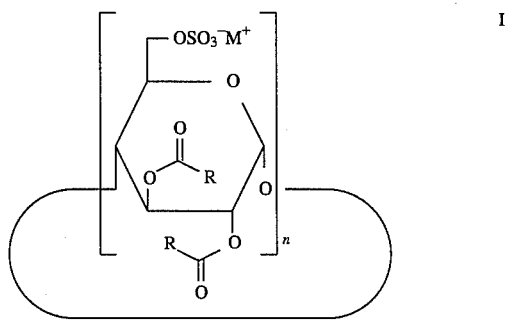

where:

M is a pharmaceutically acceptable cation;

R is selected from the group consisting of $C_1$–$C_{12}$ lower alkyl, $C_3$–$C_{12}$ cycloalkyl, and aryl optionally substituted with 1–3 substituents independently selected from halogen, $C_1$–$C_{12}$ lower alkyl or $C_1$–$C_{12}$ alkoxy; and n is an integer from 6–8, representing α-cyclodextrin (n=6), β-cyclodextrin (n=7), and γ-cyclodextrin (n=8).

2. A compound according to claim 1 wherein:

M is a pharmaceutically acceptable cation;

R is selected from the group consisting of $C_1$–$C_{12}$ loweralkyl, $C_3$–$C_{12}$ cycloalkyl, and aryl; and n is an integer from 6–8, representing α-cyclodextrin (n=6), β-cyclodextrin (n=7), and γ-cyclodextrin (n=8).

3. A compound according to claim 2 wherein:

M is a pharmaceutically acceptable salt cation;

R is phenyl; and n is an integer from 6–8, representing α-cyclodextrin (n=6), β-cyclodextrin (n=7), and γ-cyclodextrin (n=8).

4. A compound according to claim 3 wherein:

M is a Na;

R is phenyl; and n is 6.

5. A method of inhibiting smooth muscle cell proliferation occuring in a mammal which comprises administering thereto a therapeutically effective amount of a compound of Formula I below:

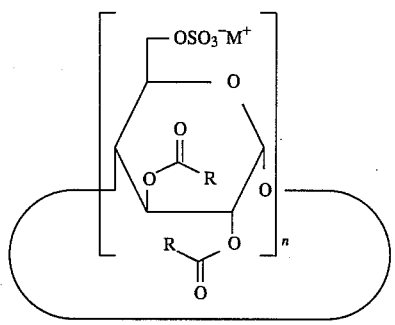

I where:
- M is a pharmaceutically acceptable cation;
- R is selected from the group consisting of $C_1$–$C_{12}$ lower alkyl, $C_3$–$C_{12}$ cycloalkyl, and aryl optionally substituted with 1–3 substituents independently selected from halogen, $C_1$–$C_{12}$ lower alkyl or $C_1$–$C_{12}$ alkoxy; and
- n is an integer from 6–8, representing α-cyclodextrin (n=6), β-cyclodextrin (n=7), and γ-cyclodextrin (n=8).

6. A method according to claim 5 where in the compound used,
- M is a pharmaceutically acceptable cation;
- R is selected from the group consisting of $C_1$–$C_{12}$ loweralkyl, $C_3$–$C_{12}$ cycloalkyl, and aryl; and
- n is an integer from 6–8, representing α-cyclodextrin (n=6), β-cyclodextrin (n=7), and γ-cyclodextrin (n=8).

7. A method according to claim 6 where in the compound used,
- M is a pharmaceutically acceptable salt cation:
- R is phenyl; and
- n is an integer from 6–8, representing α-cyclodextrin (n=6), β-cyclodextrin (n=7), and γ-cyclodextrin (n=8).

8. A method according to claim 7 wherein the compound used,
- M is a Na;
- R is phenyl; and
- n is 6.

9. A pharmaceutical composition which is comprised of a pharmaceutical carrier and a therapeutically effective amount of a compound of Formula I

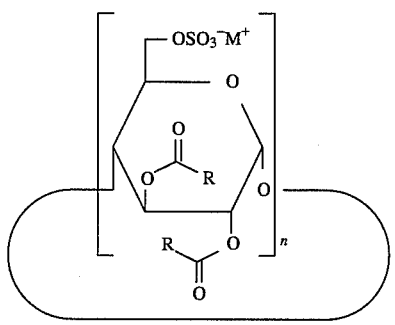

I where:
- M is a pharmaceutically acceptable cation;
- R is selected from the group consisting of $C_1$–$C_{12}$ lower alkyl, $C_3$–$C_{12}$ cycloalkyl, and aryl optionally substituted with 1–3 substituents independently selected from halogen, $C_1$–$C_{12}$ lower alkyl or $C_1$–$C_{12}$ alkoxy; and
- n is an integer from 6–8, representing α-cyclodextrin (n=6), β-cyclodextrin (n=7), and γ-cyclodextrin (n=8).

* * * * *